US005677321A

United States Patent [19]

Jeon et al.

[11] Patent Number: 5,677,321
[45] Date of Patent: Oct. 14, 1997

[54] 5- AND 6-(2-IMIDAZOLIN-2-YLAMINO) AND -(2-THIAZOLIN-2-YLAMINO)-BENZOTHIAZOLES AS ALPHA-2 ADRENERGIC LIGANDS

[75] Inventors: Yoon T. Jeon, Ridgewood; Charles Gluchowski, Wayne, both of N.J.

[73] Assignee: Synaptic Pharmaceutical Corporation, Paramus, N.J.

[21] Appl. No.: 608,598

[22] Filed: Feb. 29, 1996

[51] Int. Cl.$^6$ .................... A61K 31/425; A61K 31/415; C07D 277/82; C07D 277/62; C07D 403/02

[52] U.S. Cl. .................. 514/366; 514/367; 514/397; 548/161; 548/178; 548/181; 548/183; 548/190; 548/234; 548/312.1

[58] Field of Search .................. 548/190, 234, 548/312.1, 483, 161, 178; 514/366, 367, 397

[56] References Cited

U.S. PATENT DOCUMENTS

| | | | |
|---|---|---|---|
| 2,863,874 | 12/1958 | Gregory | 548/190 |
| 2,870,161 | 1/1959 | Bloom | 548/234 |
| 3,624,097 | 11/1971 | Strandtmann | 548/234 X |
| 3,666,767 | 5/1972 | Wittekind et al. | 548/312.1 X |
| 4,108,982 | 8/1978 | Amschler | 424/73 |
| 4,221,798 | 9/1980 | Cohnen | 424/258 |
| 4,398,028 | 8/1983 | Neumann | 544/331 |
| 4,584,385 | 4/1986 | Dirlam | 548/225 |
| 4,659,731 | 4/1987 | Bigg et al. | 514/397 |
| 4,777,181 | 10/1988 | Cohnen et al. | 514/392 |
| 4,861,789 | 8/1989 | Berge et al. | 514/370 |
| 5,521,145 | 5/1996 | Takano et al. | 504/225 |

FOREIGN PATENT DOCUMENTS

| | | |
|---|---|---|
| 0399791 | 11/1990 | European Pat. Off. . |
| 1282535 | 7/1972 | United Kingdom . |
| WO/9424105 | 10/1994 | WIPO . |
| WO/9425012 | 11/1994 | WIPO . |
| WO/9504047 | 2/1995 | WIPO . |
| WO/9519968 | 7/1995 | WIPO . |

*Primary Examiner*—Floyd D. Higel
*Attorney, Agent, or Firm*—John P. White

[57] ABSTRACT

This invention is directed to indole and benzothiazole compounds which are selective for cloned human alpha 2 receptors. This invention is also related to uses of these compounds for any indication where use of an alpha 2 agonist may be appropriate. Specifically, this includes use as analgesic, sedative and anaesthetic agents. In addition, this invention includes using such compounds for lowering intraocular pressure, presbyopia, treating migraine, hypertension, alcohol withdrawal, drug addiction, rheumatoid arthritis, ischemic pain, spasticity, diarrhea, nasal decongestion, urinary incontinence as well as for use as cognition enhancers and ocular vasoconstriction agents. The invention further provides a pharmaceutical composition comprising a therapeutically effective amount of the above-defined compounds and a pharmaceutically acceptable carrier.

16 Claims, No Drawings

5- AND 6-(2-IMIDAZOLIN-2-YLAMINO) AND -(2-THIAZOLIN-2-YLAMINO)- BENZOTHIAZOLES AS ALPHA-2 ADRENERGIC LIGANDS

Throughout this application, various references are referred to within parentheses. Disclosures of these publications in their entireties are hereby incorporated by reference into this application to describe more fully the state of the art to which this invention pertains.

BACKGROUND OF THE INVENTION

Alpha adrenergic receptors are plasma membrane receptors which are located in the peripheral and central nervous systems throughout the body. They are members of a diverse family of structurally related receptors which contain seven putative helical domains and transduce signals by coupling to guanine nucleotide binding proteins (G-proteins). These receptors are important for controlling many physiological functions and, thus, have been important targets for drug development during the past 40 years. Examples of alpha adrenergic drugs include clonidine, phenoxybenzamine and prazosin (for treatment of hypertension), naphazoline (for nasal decongestion), medetomidine (for veterinary analgesia), UK-14,304 and p-aminoclonidine (for glaucoma). However, most of these drugs produce undesirable side effects, possibly due to their interactions with other receptor subtypes. For example, clonidine is a well known centrally acting antihypertensive agent. However, it also produces untoward side effects such as analgesia, sedation, bradycardia and dry mouth which may be due to its lack of selectivity at $\alpha_2$ receptors.

α-Adrenergic receptors were originally proposed to have only two (alpha and beta) subtypes (Berthelsen, S.; Pettinger W. Life Sci., 21, 595 (1977)). However, modern molecular biological and pharmacological techniques have led to the identification of at least 6 subtypes ($\alpha_{1a}$, $\alpha_{1b}$, $\alpha_{1c}$, $\alpha_{2a}$, $\alpha_{2b}$ and $\alpha_{2c}$) of the adrenergic receptors (Bylund, D. B., Trends Pharmacol. Sci., 9, 356 (1988)).

Among many other therapeutic indications, $\alpha_2$ receptors are believed to modulate pain and behavioral depression by regulating locus coeruleus firing. In addition, $\alpha_2$ receptors are well known to be involved in effects on blood pressure, heart rate, vasoconstriction and on glaucoma. However, it is not known which therapeutic indications are controlled by each of these subtypes.

The effects of $\alpha_2$ receptor agonists on analgesia, anesthesia and sedation have been well documented for past 10 years (Pertovaara, A., Progress in Neurobiology, 40, 691 (1993)). For example, systematic administration of clonidine has been shown to produce antinociception in various species including human patients in addition to its well known sedative effects. Intrathecal and epidural administration of clonidine has also proved effective in producing antinociception. Another $\alpha_2$ agonist, medetomidine, which has better $\alpha_2/\alpha_1$ selectivity and is more potent at $\alpha_2$ receptors than clonidine, has been extensively studied for its antinociception effect. In the spinally-initiated heat-induced tail flick test in rats, systemic administration of medetomidine produced a dose-dependent antinociception which could be totally reversed by $\alpha_2$ receptor antagonists, atipamazole or idazoxan. Experimental studies of medetomidine on pain sensitivity in humans also indicated that this agent is very effective for ischemic pain, even though effective drug doses were high enough to produce sedation and considerable decreases in blood pressure.

Effects of $\alpha_2$ receptor agonists in anaesthetic practice have also been investigated (Bloor, B. C.; Flacke, W. E., Anesth. Analg., 61, 741 (1982)). The sedative effect of $\alpha_2$ agonists is regarded as good component of premedication. Another beneficial effect of $\alpha_2$ agonists in anaesthetic practice is their ability to potentiate the anaesthetic action of other agents and to reduce anaesthetic requirements of other drugs during surgery. Studies shows that premedication with 5 µg kg$^{-1}$ of oral clonidine administration reduced fentanyl requirements for induction and intubation by 45% in patients undergoing aortocoronary bypass surgery (Ghingnone, M., et al., Anesthesiology, 64, 36 (1986)).

SUMMARY OF THE INVENTION

This invention is directed to novel indole and benzothiazole compounds which are selective for cloned human $\alpha_2$ adrenergic receptors. This invention is also related to uses of these compounds for any indication where use of an $\alpha_2$ adrenergic receptor agonist may be appropriate. Specifically, this includes use as analgesic, sedative and anaesthetic agents. In addition, this invention includes using such compounds for lowering intraocular pressure, treating migraine headache, hypertension, presbyopia, alcohol withdrawal, drug addiction, rheumatoid arthritis, ischemia, spasticity, diarrhea, nasal decongestion, urinary incontinence as well as for use as cognition enhancers and ocular vasoconstriction agents. The invention further provides a pharmaceutical composition comprising a therapeutically effective amount of the above-defined compounds and a pharmaceutically acceptable carrier.

DETAILED DESCRIPTION OF THE INVENTION

The present invention is directed to compounds having the structure:

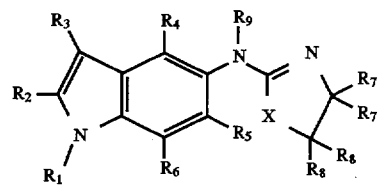

where each of $R_1$, $R_2$ and $R_3$ is independently —H; straight chained or branched $C_1$–$C_7$ alkyl, monofluoroalkyl or polyfluoroalkyl; straight chained or branched $C_2$–$C_7$ alkenyl or alkynyl;

where each of $R_4$, $R_5$ and $R_6$ is independently —H, —F, —Cl, —Br, —I, —OH, —OR$_7$, —OCOR$_7$, —SR$_7$, —N(R$_7$)$_2$, —CN, —CO$_2$R$_7$, —CON(R$_7$)$_2$, or —COR$_7$; straight chained or branched $C_1$–$C_7$ alkyl, monofluoroalkyl or polyfluoroalkyl; straight chained or branched $C_2$–$C_7$ alkenyl or alkynyl; $C_3$–$C_3$cycloalkyl or cycloalkenyl; $C_4$–$C_7$ heterocycloalkyl or heteroaryl; phenyl, substituted phenyl or phenyl substituted $C_1$–$C_4$ alkyl where the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

where each of $R_7$ is independently —H; —N(R$_{10}$)$_2$, —NR$_{10}$COR$_{10}$, —(CH$_2$)$_n$OR$_{10}$, —SO$_n$R$_{10}$, —SO$_n$N(R$_{10}$)$_2$, —(CH$_2$)$_n$N(R$_{10}$)$_2$, or —(CH$_2$)$_n$NR$_{10}$COR$_{10}$; straight chained or branched $C_1$–$C_7$ alkyl; straight chained or branched $C_2$–$C_7$ alkenyl or alkynyl; phenyl, substituted phenyl or phenyl substituted $C_1$–$C_4$ alkyl where the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

where each n is independently an integer from 1 to 4;

where each R$_8$ is independently —H; straight chained or branched $C_1$–$C_7$ alkyl; straight chained or branched $C_2$–$C_7$ alkenyl or alkynyl; $C_3$–$C_7$ cycloalkyl or cycloalkenyl; phenyl, substituted phenyl or phenyl substituted $C_1$–$C_4$ alkyl where the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

where R$_9$ is independently —H; straight chained or branched $C_1$–$C_7$ alkyl; straight chained or branched $C_2$–$C_7$ alkenyl or alkynyl; $C_3$–$C_7$ cycloalkyl or cycloalkenyl; $C_4$–$C_7$ heterocycloalkyl or heteroaryl; phenyl, substituted phenyl or phenyl substituted $C_1$–$C_4$ alkyl where the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

where each R$_{10}$ is independently —H; straight chained or branched $C_1$–$C_7$ alkyl; straight chained or branched $C_2$–$C_7$ alkenyl or alkynyl; and where X is independently CH$_2$, O, NH or S; or a pharmaceutically acceptable salt thereof.

Note that when R$_9$ is H, the H undergoes exchange between the adjacent amine and imidazole nitrogen atoms, in a phenomenon called "tautomerization." Throughout this application, the pictorial representation of this structure where R$_9$ is H places the exchangeable H on the amine nitrogen atom.

In a preferred embodiment, the compounds may have the structure:

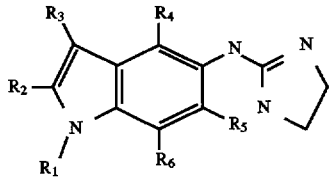

where R$_1$, R$_2$, R$_3$, R$_4$, R$_5$, and R$_6$ are as defined above.

In preferred embodiments, the invention includes compounds having the structures:

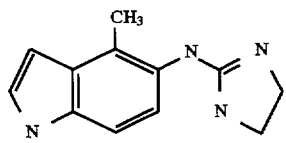

EXAMPLE 1

4-Methyl-5-(2-imidazolin-2-ylamino)indole

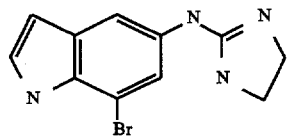

EXAMPLE 2

7-Bromo-5-(2-imidazolin-2-ylamino)indole

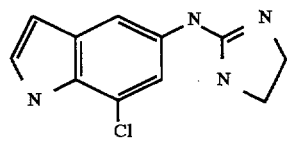

EXAMPLE 3

7-Chloro-5-(2-imidazolin-2-ylamino)indole

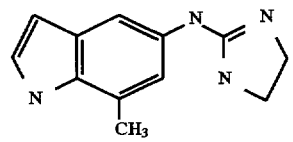

EXAMPLE 4

7-Methyl-5-(2-imidazolin-2-ylamino)indole

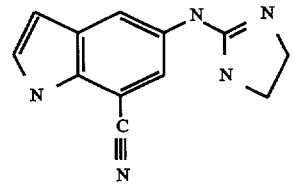

EXAMPLE 5

7-Cyano-5-(2-imidazolin-2-ylamino)indole

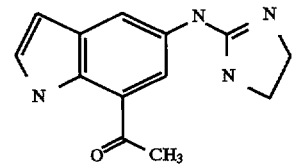

EXAMPLE 6

7-Acetyl-5-(2-imidazolin-2-ylamino)indole

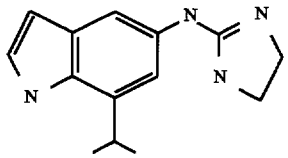

EXAMPLE 10

7-Isopropanyl-5-(2-imidazolin-2-ylamino)indole.

In another embodiment, the compounds may have the structures:

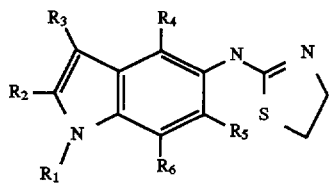

where $R_1$, $R_2$, $R_3$, $R_4$, $R_5$, and $R_6$ are as defined above.

Another embodiment of the invention includes the compound having the following structure:

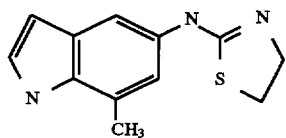

EXAMPLE 8

7-Methyl-5-(2-thiazolin-2-ylamino)indole

In still another embodiment, the compounds may have the structure:

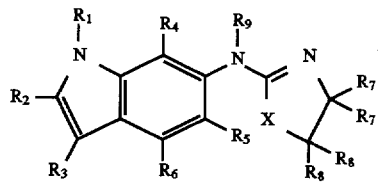

where $R_1$, $R_2$, $R_3$, $R_4$, $R_5$, $R_6$, $R_7$, $R_8$, $R_9$, and X are as defined above.

In one embodiment, the compounds may have the structure:

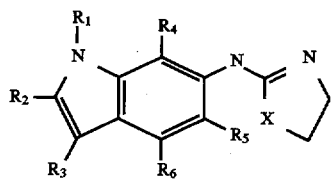

where $R_1$, $R_2$, $R_3$, $R_4$, $R_5$, $R_6$, and X are as defined above.

In another embodiment, the compounds may have the structures:

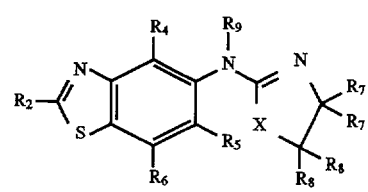

where $R_2$, $R_4$, $R_5$, $R_6$, $R_7$, $R_8$, $R_9$, and X are as defined above.

In another embodiment, the compounds may have the structure:

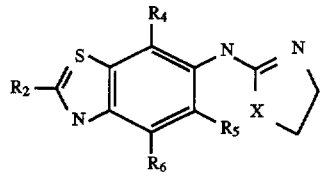

where $R_2$, $R_4$, $R_5$, $R_6$, and X are as defined above.

In one preferred embodiment, the compound may have the structure:

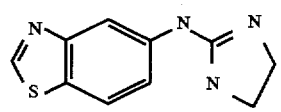

EXAMPLE 13

5-(2-Imidazolin-2-ylamino)benzothiazole.

In another embodiment, the compounds may have the structure:

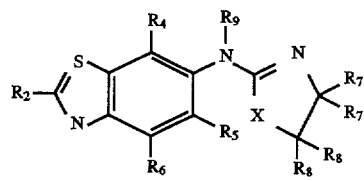

where $R_2$, $R_4$, $R_5$, $R_6$, $R_7$, $R_8$, $R_9$, and X are as defined above.

In another embodiment, the compounds may have the structure:

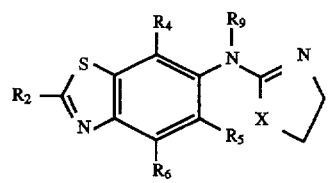

where $R_2$, $R_4$, $R_5$, $R_6$, $R_9$, and X are as defined above.

In one preferred embodiment, the compound may have the structure:

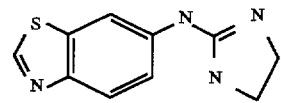

EXAMPLE 14

6-(2-Imidazolin-2-ylamino)benzothiazole

In another preferred embodiment, the compound may have the structure:

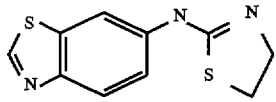

EXAMPLE 15

6-(2-Thiazolin-2-ylamino)benzothiazole

The invention also provides for the (−) and (+) enantiomers of the compounds of the subject application described herein. Included in this invention are pharmaceutically acceptable salts and complexes of all of the compounds described herein. The salts include but are not limited to the following acids and bases. The following inorganic acids; hydrochloric acid, hydrofluoric acid, hydrobromic acid, hydroiodic acid, sulfuric acid and boric acid. The organic acids; acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid. The following inorganic bases; ammonia, hydroxyethylamine and hydrazine. The following organic bases; methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The invention also provides a pharmaceutical composition comprising a therapeutically effective amount of the compounds described above and a pharmaceutically acceptable carrier. In the subject invention a "therapeutically effective amount" is any amount of a compound which, when administered to a subject suffering from a disease against which the compounds are effective, causes reduction, remission, or regression of the disease. In one embodiment the therapeutically effective amount is an amount from about 0.01 mg per subject per day to about 500 mg per subject per day, preferably from about 0.1 mg per subject per day to about 50 mg per subject per day and most preferably from about 1 mg per subject per day to about 20 mg per subject per day. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

The invention further provides a method for anaesthetic premedication which comprises administering to the subject an amount of any of the compounds described above effective to reduce in the subject the requirement for anaesthetic drugs.

The invention further provides a method for sedating a subject which comprises administering to the subject an amount of any of the compounds described above effective to sedate the subject.

This invention also provides a method for ocular vasoconstriction in a subject which comprises administering to the subject an amount of any of the compounds described above effective to produce ocular vasoconstriction in the subject.

This invention also provides a method of treating a subject suffering from a disorder associated with elevated intraocular pressure which comprises administering to the subject an amount of any of the compounds described above effective to lower the subject's intraocular pressure.

This invention also provides a method of treating a subject suffering from migraine headache which comprises administering to the subject an amount of any of the compounds described above effective to treat the subject's migraine headache.

This invention also provides a method of treating a subject suffering from hypertension which comprises administering to the subject an amount of any of the compounds described above effective to treat the subject's hypertension.

This invention also provides a method of treating a subject suffering from alcohol withdrawal which comprises administering to the subject an amount of any of the compounds described above effective to treat the subject's alcohol withdrawal.

This invention also provides a method of treating a subject suffering from drug addiction which comprises administering to the subject an amount of any of the compounds described above effective to treat the subject's drug addiction.

This invention also provides a method of treating a subject suffering from rheumatoid arthritis which comprises administering to the subject an amount of any of the compounds described above effective to treat the subject's rheumatoid arthritis.

This invention also provides a method of treating a subject suffering from presbyopia which comprises administering to the subject an amount of any of the compounds described above effective to treat the subject's presbyopia.

This invention also provides a method of treating a subject suffering from ischemic pain which comprises administering to the subject an amount of any of the compounds described above effective to treat the subject's ischemic pain.

This invention also provides a method of treating a subject suffering from spasticity which comprises administering to the subject an amount of any of the compounds described above effective to treat the subject's spasticity.

This invention also provides a method of treating a subject suffering from diarrhea which comprises administering to the subject an amount of any of the compounds described above effective to treat the subject's diarrhea.

This invention also provides a method of treating a subject suffering from nasal congestion which comprises administering to the subject an amount of any of the compounds described above effective to treat the subject's nasal congestion.

This invention also provides a method of treating a subject suffering from urinary incontinence which comprises administering to the subject an amount of any of the compounds described above effective to treat the subject's urinary incontinence.

This invention also provides a method of treating a disease which is susceptible to treatment by agonism of the $\alpha_2$ adrenergic receptor which comprises administering to the subject an amount of any of the compounds described above effective to treat the disease.

This invention also provides a method of treating a subject suffering from pain which comprises administering to the subject an amount of any of the compounds described above effective to treat the subject's pain.

One skilled in the art will readily appreciate that appropriate biological assays will be used to determine the therapeutic potential of the claimed compounds for treating the above noted disorders.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

The compounds claimed have been prepared using the synthetic sequences shown in Schemes 1–6. Detailed synthetic procedures for specific compounds are as described in the Examples below. All NMRS were obtained using a 300 MHz GE QEPLUS NMR machine.

Pharmacological profiles of the claimed compounds at cloned human alpha adrenergic receptors were determined in vitro binding and functional assays using cultured cell lines that selectively express the receptor of interest. Equilibrium competition binding assays were performed with membrane preparations from cultured LM(tk⁻) cells stably transfected with the cloned human alpha adrenoreceptor subtypes except for $\alpha_{2b}$, which was expressed in Y-1 cells, using [$^3$H] prazosin for $\alpha_1$ receptors and [$^3$H] rauwolscine for $\alpha_2$ receptors. Further details of pharmacological evaluations of claimed compounds are described in Example 21.

EXAMPLE 1

4-Methyl-5-(2-imidazolin-2-ylamino)indole

4-Methyl-5-nitroindole

To a solution of 5-nitroindole (from Aldrich, 0.82 g, 5.1 mmol) in 20 mL of dry THF was added 5.0 mL (15 mmol) of methylmagnesium bromide for 0.5 h period and the resulting reaction mixture was stirred for 1 h at 25° C. Reaction was the quenched by adding a THF solution of tetrachloro-1,4-benzoquinone (1.2 g, 4.9 mmol). Reaction mixture was concentrated in vacuo, yielding a dark solid which was subjected to column chromatography (30% EtOAc/n-Hexane) to yield 0.72 g (4.1 mmol, 80%) of the desired product.

4-Methyl-5-aminoindole

A solution of 4-methyl-5-nitroindole (0.72 g, 4.1 mmol) in 50 mL of methanol was stirred with 50 mg of 10% Pd/C under H$_2$ for 12 h. Reaction mixture was filtered and concentrated in vacuo to provide an oil (0.61 g, >95%) which was characterized as the desired product by NMR analysis and subjected to a following reaction without further purification.

2-Imidazoline-2-sulfonic acid (ISA)

ISA was prepared according to the procedure described in literature (Gluchowski, C. U.S. Pat. No. 5,130,441, 1992). To a solution of 2-imidazolinethione (6.6 g, 65 mmol), sodium molybdate(IV) dihydrate (0.5 g, 2.1 mmol) and NaCl (1.5 g) in 150 mL of distilled water was added 30% of $H_2O_2$ (50 mL, 450 mmol) for 1 h at $-10°$ C. The reaction mixture was stored at $-20°$ C. for 12 h and then reaction temperature was slowly warmed up to 25° C. The white crystal obtained was filtered and dried in vacuo to provide 2.8 g (21 mmol, 32%) of the acid. The compound was used in many of the examples noted below.

4-Methyl-5-(2-imidazolin-2-ylamino)indole

The amine (0.61 g, 4.1 mmol) and ISA (1.0 g, 7.6 mmol) in 10 mL of isobutanol were stirred at reflux for 12 h. The reaction mixture was concentrated in vacuo, providing an oily residue which was purified on column chromatography (20% $NH_3$ saturated MeOH/EtOAc) to yield 0.52 g (2.4 mmol, 59%) of the desired product. The product obtained was converted to the fumarate salt and recrystallized from isopropanol to afford 0.37 g (27%) of the product as a light brown solid: mp 215°–218° C.; $^1$H NMR ($CD_3OD$) $\delta$7.28 (d, J=1.8 Hz, 1H), 7.25 (d, J=3.3 Hz, 1H), 6.92 (d, J=3.3 Hz, 1H), 6.52 (d, J=1.8 Hz, 1H), 3.68 (s, 4H), 2.42(s, 3H); Anal. Calc. for $C_{12}H_{14}N_4 \cdot 1.0C_4H_4O_4$ requires C, 58.18; H, 5.49; N, 16.96. Found: C, 58.87; H, 5.44; N, 16.77.

EXAMPLE 2

7-Bromo-5-(2-imidazolin-2-ylamino)indole

7-Bromo-5-nitroindoline

To a solution of 5-nitroindoline (from Aldrich, 2.0 g, 12.2 mmol) in 15 mL of AcOH was added $Br_2$ (1.0 mL, 19.4 mmol) in a portion and the resulting solution was stirred for 1 h at 25° C. Reaction mixture was concentrated in vacuo, yielding a yellow solid (3.9 g, >95%) of the desired product as a HBr salt, which was subjected to the following reaction without further purification.

7-Bromo-5-nitroindole

To a solution of 7-bromo-5-nitroindoline (3.0 g, 12.3 mmol) in 200 mL of acetone was added 2,3-dichloro-5,6-dicyano-1,4-benzoquinone until color of the solution turns to dark green. The reaction mixture was concentrated in vacuo and subjected to column chromatography ($CHCl_3$, neat) to yield 2.7 g (11.2 mmol, 91%) of the indole.

7-Bromo-5-aminoindole

A solution of 7-bromo-5-nitroindole (0.68 g, 2.8 mmol), hydrazine (1.0 mL, 31 mmol) and 10% Pd/C (50 mg) in 50 mL of isopropanol was stirred at reflux for 2 h. The reaction mixture was filtered and concentrated in vacuo, yielding oily residue which was subjected to column chromatography ($CHCl_3$, neat) to produce 0.41 g (2.0 mmol, 70%) of the desired product.

7-Bromo-5-(2-imidazolin-2-ylamino)indole

The amine (0.41 g, 2.0 mmol) and ISA (0.65 g, 4.9 mmol) were stirred at reflux for 12 h. The reaction mixture was concentrated in vacuo, yielding an oil which was purified on column chromatography (20% $NH_3$ saturated MeOH/ EtOAc) to yield 0.26 g (0.91 mmol, 46%) of the desired product. The product obtained was converted to the fumarate salt and recrystallized from isopropanol to afford 0.21 g (21%) of the product as a white solid: mp 272°–273° C.; $^1$H NMR ($CD_3OD$) $\delta$7.45 (d, J=1.8 Hz, 1H), 7.36 (d, J=3.3 Hz, 1H), 7.20 (d, J=1.8 Hz, 1H), 6.56 (d, J=3.2 Hz, 1H), 3.68 (s, 4H); Anal. Calc. for $C_{11}H_{11}BrN_4 \cdot 2.0C_4H_4O_4$ requires C, 44.63; H, 3.75; N, 10.96. Found: C, 45.25; H, 3.73; N, 11.53.

EXAMPLE 3

7-Chloro-5-(2-imidazolin-2-ylamino)indole

7-Chloro-5-nitroindoline

To a solution of 5-nitroindoline (0.5 g, 3.1 mmol) in 15 mL of AcOH was added a solution of $Cl_2$ in AcOH dropwise until 30% of starting material was consumed. The reaction mixture was concentrated in vacuo, yielding an oil which was subjected to column chromatography ($CHCl_3$, neat) to provide 0.23 g (1.2 mmol) of the desired product.

7-Chloro-5-nitroindole

To a solution of 7-chloro-5-nitroindoline (0.23 g, 1.2 mmol) in 20 mL of acetone was added 2,3-dichloro-5,6-dicyano-1,4-benzoquinone until color of the solution turns to dark green. Reaction mixture was concentrated in vacuo providing a dark residue which was subjected to column chromatography ($CHCl_3$, neat) to yield 0.18 g (0.94 mmol, 79%) of the indole.

7-Chloro-5-aminoindole

A solution of 7-chloro-5-nitroindole (0.18 g, 0.94 mmol), hydrazine (0.25 mL, 7.7 mmol) and 10% Pd/C (10 mg) in 10 mL of methanol was stirred at reflux for 2 h. The reaction mixture was filtered and concentrated in vacuo, yielding an oil (0.16 g, >95%), which was characterized as the desired product by NMR analysis and subjected to the following reaction without further purification.

7-Chloro-5-(2-imidazolin-2-ylamino)indole

The amine (0.16 g, 0.95 mmol) and ISA (0.30 g, 2.2 mmol) was stirred at reflux for 12 h. The reaction mixture was concentrated in vacuo, yielding an oil which was purified on column chromatography (20% $NH_3$ saturated MeOH/EtOAc) to yield 0.16 g (0.56 mmol, 59%) of the desired product. The product obtained was converted to the fumarate salt and recrystallized from isopropanol to afford 0.17 g (86%) of the product as a white solid: mp 261°–262° C.; $_1$H NMR ($CD_3OD$) $\delta$7.41 (d, J=1.8 Hz, 1H), 7.36 (d, J=3.3 Hz, 1H), 7.05 (d, J=1.8 Hz, 1H), 6.35 (d, J=3.2 Hz, 1H), 3.68 (s, 4H); Anal. Calc. for $C_{11}H_{11}ClN_4 \cdot 1.0C_4H_4O_4$ requires C, 51.36; H, 4.31; N, 15.97. Found: C, 51.68; H, 4.41; N, 15.52.

EXAMPLE 4

7-Methyl-5-(2-imidazolin-2-ylamino)indole

7-Methyl-5-nitroindole

To a solution of 7-bromo-5-nitroindoline (0.65 g, 2.7 mmol) in 10 mL of DMF were added tetramethyltin (1.0 mL, 7.3 mmol) and bis(triphenylphosphine)palladium(II) chloride (0.10 g) in a portion and resulting mixture was stirred in sealed tube for 12 h at 140° C. The reaction mixture was concentrated in vacuo, providing a dark oily residue which was subjected to column chromatography ($CHCl_3$, neat) to yield 0.35 g (2.0 mmol, 74%) of the desired product.

7-Methyl-5-aminoindole

A solution of 7-methyl-5-nitroindole (0.35 g, 2.0 mmol) and 10% Pd/C (50 mg) in 20 mL of MeOH was stirred under $H_2$. The reaction mixture was filtered and concentrated in vacuo, yielding an oil (0.16 g, 1.1 mmol, 41%), which was characterized by NMR and subjected to the following reaction without further purification.

7-Methyl-5-(2-imidazolin-2-ylamino)indole

The amine (0.16 g, 1.1 mmol) and ISA (0.30 g, 2.2 mmol) in 10 mL of isobutanol was stirred at reflux for 12 h. The reaction mixture was concentrated in vacuo, yielding oily residue which was purified on column chromatography (20% $NH_3$ saturated MeOH/EtOAc) to provide 0.16 g (0.75 mmol, 68%) of the desired product. The product obtained was converted to the fumarate salt and recrystallized from isopropanol to afford 0.21 g (93%) of the product as a white solid: mp 224°–226° C.; $^1$H NMR ($CD_3OD$) $\delta$7.27 (d, J=1.8 Hz, 1H), 7.26 (d, J=3.3 Hz, 1H), 6.76 (d, J=1.8 Hz, 1H), 6.44

(d, J=3.3 Hz, 1H), 3.67 (s, 4H), 2.47 (s, 3H); Anal. Calc. for $C_{12}H_{14}N_4 \cdot 1.0C_4H_4O_4$ requires C, 58.17; H, 5.49; N, 16.96. Found: C, 58.11; H, 5.40; N, 16.40.

EXAMPLE 5

7-Cyano-5-(2-imidazolin-2-ylamino)indole

7-Cyano-5-nitroindole

A solution of 7-bromo-5-nitroindole (2.5 g, 10.4 mmol), CuCN (3.0 g, 33.3 mmol) and KCN (3.0 g, 46.1 mmol) in 20 mL of DMF was stirred at 120° C. for 24 h. The reaction mixture was diluted with 500 mL of EtOAc and washed with brine several times. Organic layer was dried over $Na_2SO_4$ and concentrated in vacuo, yielding a brown oily residue which was subjected to column chromatography ($CHCl_3$, neat) to provide 1.5 g (8.2 mmol, 77%) of the desired product.

7-Cyano-5-aminoindole

A solution of 7-cyano-5-nitroindole (1.5 g, 8.2 mmol), hydrazine (1.0 mL, 31.2 mmol) and 10% Pd/C (20 mg) in 30 mL of MeOH was stirred at reflux for 2 h. The reaction mixture was filtered and concentrated in vacuo to provide 1.3 g (>95%) of the amine.

7-Cyano-5-(2-imidazolin-2-ylamino)indole

The amine (0.11 g, 0.70 mmol) and ISA (0.20 g, 1.4 mmol) in 10 mL of isobutanol was stirred at reflux for 12 h. The reaction mixture was concentrated in vacuo, providing oily residue which was purified on column chromatography (20% $NH_3$ saturated MeOH/EtOAc) to yield 0.13 g (0.57 mmol, 82%) of the desired product. The product obtained was converted to the fumarate salt and recrystallized from MeOH to afford 0.02 g of the product as a white solid: mp 290°–295° C.; $^1H$ NMR (DMSO-D6) $\delta$7.64 (d, J=1.8 Hz, 1H), 7.47 (d, J=3.2 Hz, 1H), 7.37 (d, J=1.8 Hz, 1H), 6.55 (d, J=3.2 Hz, 1H), 3.51(s, 4H).

EXAMPLE 6

7-Acetyl-5-(2-imidazolin-2-ylamino)indole

7-Acetyl-5-nitroindole

To a solution of 7-cyano-5-nitroindole (0.7 g, 4.4 mmol) in 20 mL of THF was added 5.0 mL of MeMgBr (3.0M) and the resulting reaction mixture was stirred for 12 h at 25° C. Reaction was quenched by adding 10 mL of 1.0N aqueous HCl. Reaction mixture was basified with 3N aqueous NaOH and aqueous solution was extracted with EtOAc several times. Organic extracts were dried over $MgSO_4$ and concentrated in vacuo to provide oily residue which was subjected to column chromatography (50% EtOAc/Cy.hexane) to yield 0.20 g (1.2 mmol, 26%) of the desired product.

7-Acetyl-5-aminoindole

A solution of 7-acetyl-5-nitroindole (0.2 g, 1.2 mmol) and 10% Pd/C (30 mg) in 20 mL of MeOH was stirred at reflux for 1 h. The reaction mixture was filtered and concentrated in vacuo, yielding oil (0.17 g, >95%), which was characterized by NMR and subjected to the following reaction without further purification.

7-Acetyl-5-(2-imidazolin-2-ylamino)indole

The amine (0.17 g, 1.2 mmol) and ISA (0.30 g, 2.2 mmol) were stirred at reflux for 12 h. The reaction mixture was concentrated in vacuo, yielding an oil which was purified on column chromatography (20% $NH_3$ saturated MeOH/EtOAc) to yield 0.08 g (0.33 mmol, 28%) of the desired product. The product obtained was converted to the fumarate salt and recrystallized from MeOH to afford 0.03 g of the product as a white solid: mp 238°–240° C.; $^1H$ NMR (CD$_3$OD) $\delta$7.77 (d, J=2.1 Hz, 1H), 7.72 (d, J=2.1 Hz, 1H), 7.41 (d, J=3.3 Hz, 1H), 6.56 (d, J=3.2 Hz, 1H), 3.70 (s, 4H).

EXAMPLE 7

7-Amido-5-(2-imidazolin-2-ylamino)indole 7-amido-5-nitroindole

To a solution of 7-cyano-5-nitroindole (0.30 g, 1.9 mmol) in 5 mL of MeOH was added 5.0 mL of $NH_4OH$ and 2 mL of $H_2O_2$, and the resulting reaction mixture was stirred for 12 h at 25° C. Reaction was concentrated in vacuo to get rid of MeOH. Remaining aqueous layer was then extracted with EtOAc several times. The organic extracts were dried over $MgSO_4$ and concentrated in vacuo to provide an oil (0.27 g, >95%) which was identified as the desired product by NMR analysis and subjected to the following reaction without further purification.

7-Amido-5-aminoindole

A solution of 7-acetyl-5-nitroindole (0.28 g, 1.9 mmol), hydrazine (1.0 mL) and 10% Pd/C (30 mg) in 20 mL of MeOH was stirred at reflux for 1 h. The reaction mixture was filtered and concentrated in vacuo, yielding an oil (0.23 g, >95%), which was characterized as the amine by NMR analysis and subjected to a following reaction without further purification.

7-Amido-5-(2-imidazolin-2-ylamino)indole

The amine (0.23 g, 1.9 mmol) and ISA (0.50 g, 3.7 mmol) were stirred at reflux for 12 h. The reaction mixture was concentrated in vacuo, yielding an oil which was purified on column chromatography (20% $NH_3$ saturated MeOH/EtOAc) to yield 0.21 g (0.86 mmol, 45%) of the desired product. The product obtained was converted to the fumarate salt and recrystallized from MeOH to afford 0.22 g of the product as a white solid: mp 238°–241° C.; $^1H$ NMR (CD$_3$OD) $\delta$7.55 (d, J=1.8 Hz, 1H), 7.52 (d, J=1.8 Hz, 1H), 7.40 (d, J=3.3 Hz, 1H), 6.52 (d, J=3.2 Hz, 1H), 3.72 (s, 4H); Anal. Calc. for $C_{12}H_{13}N_5O \cdot 1.0C_4H_4O_4$ requires C, 53.48; H, 4.77; N, 19.49. Found: C, 52.80; H, 4.86; N, 19.50.

EXAMPLE 8

7-Methyl-5-(2-thiazolin-2-ylamino)indole

To a solution of 7-methyl-5-aminoindole (0.70 g, 4.8 mmol) in 30 mL of chloroform and 20 mL of $NaHCO_3$ saturated aqueous solution was added thiophosgene (0.80 mL, 11 mmol) and the resulting reaction mixture was stirred for 1 h at 25° C. Organic layer was separated and concentrated in vacuo to provide an oil (0.75 g, >95%), which was identified as the isothiocyanate in NMR analysis. The isothiocyanate was dissolved in 10 mL of MeOH with chloroethylamine.HCl (1.0 g, 8.7 mmol) and $NaHCO_3$ (2.5 g, 24 mmol) and the resulting mixture was stirred at reflux for 12 h. Reaction mixture was filtered and concentrated in vacuo to provide an oil which was subjected to column chromatography (5% $NH_3$ saturated MeOH-30% EtOAc/Hex) to yield 0.31 g (1.4 mmol, 28%, overall) of the desired product. The product obtained was converted to the fumarate salt and recrystallized from EtOH to afford 0.28 g of the product as a white solid: mp 200°–202° C.; $^1H$ NMR (CD$_3$OD) $\delta$7.39 (d, J=1.8 Hz, 1H), 7.37 (d, J=3.2 Hz, 1H), 6.83 (d, J=1.8 Hz, 1H), 6.52 (d, J=3.2 Hz, 1H), 4.00 (t, 2H), 3.36 (t, 2H) ; Anal. Calc. for $C_{12}H_{13}N_3S \cdot 1.0C_4H_4O_4$ requires C, 55.32; H, 4.93; N, 12.10. Found: C, 55.60; H, 4.89; N, 12.34.

EXAMPLE 9

7-Isopropenyl-5-(2-imidazolin-2-ylamino)indole

7-Isopropenyl-5-aminoindole.

To a solution of methyltriphenylphosponium bromide (3.8 g, 10 mmol) in 40 mL of THF was added 15 mL of a solution of lithium bis(trimethylsilyl)amide (15 mmol) and the resulting reaction mixture was stirred for 1 h at −78° C. A solution of 5-amino-7-acetylindole (0.55 g, 3.1 mmol) in 10 mL of THF was added into the solution slowly for 0.5 h period. The reaction mixture was slowly warmed to 25° C. and stirred for 12 h at the temperature. Column chromatographic separation of reaction mixture (50% EtOAc/n-Hexane) provided 0.45 g (2.6 mmol, 82%) of the desired product.
7-Isopropenyl-5-(2-imidazolin-2-ylamino)indole.

A mixture of the amine 0.45 g (2.6 mmol) and ISA (0.70 g, 5.2 mmol) was dissolved in 10 mL of isobutanol and the resulting reaction mixture was stirred at reflux for 2 h. Reaction mixture was concentrated in vacuo to yield an oil, which was subjected to column chromatography (30% $NH_3$ saturated MeOH/EtOAc) to yield 0.39 g (1.6 mmol, 63%) of the desired product. The product obtained was converted to the maleate salt and recrystallized from EtOH—$CHCl_3$ to afford 0.17 g of the product as a dark brown solid: mp 154°–156° C.; H NMR ($CD_3OD$) δ7.36 (d, J=1.8 Hz, 1H), 7.28 (d, J=3.2 Hz, 1H), 6.89 (d, J=1.8 Hz, 1H), 6.48 (d, J=3.2 Hz, 1H), 5.36 (s, 1H), 5.32 (s, 1H), 3.67 (s, 4H), 2.18 (s, 3H); Anal. Calc. for $C_{14}H_{16}N_4 \cdot 1.0C_4H_4O_4$ requires C, 60.67; H, 5.66; N, 15.72. Found: C, 59.63; H, 5.63; N, 15.55.

EXAMPLE 10

7-Isopropanyl-5-(2-imidazolin-2-ylamino)indole.

A solution of 7-isopropenyl-5-(2-imidazolin-2-ylamino) indole (0.25 g, 1.0 mmol) and 10% Pd/C (100 mg) in 10 mL of MeOH was stirred for 12 h under $H_2$ (18 psi). The reaction mixture was filtered and concentrated in vacuo, yielding an oil which, in NMR analysis, was highly pure and corresponds to the desired product. The product obtained was converted to the succinate salt and recrystallized from isopropanol-$CHCl_3$ to afford 0.13 g of the product as a light brown solid: mp 254°–255° C.; H NMR ($CD_3OD$) δ7.28 (d, J=1.8 Hz, 1H), 7.27 (d, J=3.2 Hz, 1H), 6.82 (d, J=1.8 Hz, 1H), 6.43 (d, J=3.2 Hz, 1H), 3.67 (s, 4H), 3.30 (hep, 1H), 2.18 (s, 3H); Anal. Calc. for $C_{14}H_{18}N_4 \cdot 1.0C_4H_6O_4$ requires C, 60.32; H, 6.19; N, 15.63. Found: C, 60.17; H, 6.25; N, 15.59.

EXAMPLE 11

7-(2-E-2'-Butenyl)-5-(2-imidazolin-2-ylamino) indole 7-(2-E-2'-butenyl)-5-aminoindole.

To a solution of ethyltriphenylphosphonium bromide (2.6 g, 7.0 mmol) in 30 mL of THF was added 10 mL of a solution of lithium bis(trimethylsilyl)amide (10 mmol) and the resulting reaction mixture was stirred for 1 h at −78° C. A solution of 5-amino-7-acetylindole (0.31 g, 1.8 mmol) in 10 mL of THF was added into the solution slowly for 0.5 h period. The reaction mixture was slowly warmed to 25° C. and stirred for 12 h at the temperature. Column chromatographic separation of reaction mixture (50% EtOAc/n-Hexane) provided 0.29 g (1.6 mmol, 89%) of the desired product.
7-(2-E-2'-Butenyl)-5-(2-imidazolin-2-ylamino)indole.

A mixture of the amine (0.29 g, 1.6 mmol) and ISA (0.5 g, 3.7 mmol) was dissolved in 10 mL of isobutanol and the resulting reaction mixture was stirred at reflux for 2 h. Reaction mixture was concentrated in vacuo to yield an oil, which was subjected to column chromatography (30% $NH_3$ saturated MeOH/EtOAc) to yield 0.41 g (1.6 mmol, >95%) of the desired product. The product obtained was converted to the maleate salt and recrystallized from EtOH—$CHCl_3$ to afford 0.21 g of the product as a light brown solid: mp 154°–156° C.; H NMR ($CD_3OD$) δ7.30 (d, J=1.8 Hz, 1H), 7.25 (d, J=3.2 Hz, 1H), 6.78 (d, J=1.8 Hz, 1H), 6.45 (d, J=3.2 Hz, 1H), 5.81 (t, J=6.6 Hz, 1H), 3.67 (s, 4H), 2.04 (s, 3H), 1.81 (d, J=6.6 Hz, 3H); Anal. Calc. for $C_{15}H_{18}N_4 \cdot 1.0C_4H_4O_4$ requires C, 61.61; H, 5.99; N, 15.13. Found: C, 60.99; H, 6.09; N, 14.91.

EXAMPLE 12

7-Isobutanyl-5-(2-imidazolin-2-ylamino)indole.

A solution of 7-(2-E-2'-butenyl)-5-(2-imidazolin-2-ylamino)indole (0.17 g, 0.66 mmol) and 10% Pd/C (20 mg) in 10 mL of MeOH was stirred for 12 h under $H_2$ (18 psi). The reaction mixture was filtered and concentrated in vacuo, yielding an oil which, in NMR analysis, was highly pure and corresponds to the desired product. The product obtained was converted to the succinate salt and recrystallized from Isopropanol-$CHCl_3$ to afford 0.045 g of the product as a light brown solid.

EXAMPLE 13

5-(2-Imidazolin-2-ylamino)benzothiazole

5-Nitrobenzothiazole

A solution of 2-chloro-5-nitroaniline (5.0 g, 29 mmol) in 30 mL solution of 1:1 mixture of formic acid-acetic anhydride was stirred at reflux for 3 h. The reaction mixture was concentrated in vacuo to provide an oil, which was dissolved in 20 mL of DMF with $Na_2S \cdot 9H_2O$ (10 g, 42 mmol) and stirred at reflux for 2 h. The reaction mixture was diluted in 200 mL of EtOAc and washed with brine several times. Organic layer was dried over $Na_2SO_4$ and concentrated in vacuo to provide an oil which was purified on column chromatography (50% EtOAc/n-Hex.) to yield 1.2 g (6.7 mmol, 23% overall) of the desired product.
5-Aminobenzothiazole To a solution of $SnCl_2$ (7.0 g, 8.8 mmol) and 14 mL of con.HCl was added 5-nitrobenzothiazole (0.65 g, 3.6 mmol) in a portion and resulting reaction mixture was stirred for 1 h at 25° C. The reaction mixture was basified with aqueous NaOH and extracted with EtOAc. Combined organic layers were dried over $Na_2SO_4$ and concentrated in vacuo, yielding an oil (0.47 g, 3.2 mmol, 89%) which was identified as the amine (>95% pure) and subjected to the following reaction without further purification.
5-(2-Imidazolin-2-ylamino)benzothiazole A solution of the amine (0.60 g, 4.0 mmol) and ISA (1.0 g, 7.6 mmol) in 10 mL of isobutanol was stirred at reflux for 12 h. The reaction mixture was concentrated in vacuo, yielding oily residue which was purified on column chromatography (20% $NH_3$ saturated MeOH/EtOAc) to provide 0.71 g (3.2 mmol, 80%) of the desired product. The product obtained was converted to the fumarate salt and recrystallized from EtOH to provide 0.68 g of the product as a white solid: mp 201°–203° C.; $^1$H NMR ($CD_3OD$) δ9.31 (s, 1H), 8.13 (d, J=5.8 Hz, 1H), 7.96 (d, J=2.0 Hz, 1H), 7.38 (dd, J=2.0, 5.8 Hz, 1H), 3.76 (s, 4H); Anal. Calc. for $C_{10}H_{10}N_4S \cdot 1.0C_4H_4O_4$ requires C, 50.29; H, 4.22; N, 16.76. Found: C, 51.14; H, 4.13; N, 16.58.

EXAMPLE 14

6-(2-Imidazolin-2-ylamino)benzothiazole

6-Nitrobenzothiazole

To a 30 mL solution of 1:1 mixture of HNO₃—H₂SO₄ was added benzothiazole (7.0 mL, 53 mmol) slowly over 1 h period at −25° C. and resulting solution was stirred for 12 h. Reaction temperature was allowed to warm up to 25° C. The reaction mixture was poured into ice water to produce a yellow precipitation which was subjected to column chromatography (CHCl₃, neat) to yield 7.3 g (41 mmol, 79%) of the desired product.

6-Aminobenzothiazole

To a solution of SnCl₂ (1.5 g, 1.9 mmol) and 5 mL of con.HCl was added 6-nitrobenzothiazole (0.60 g, 3.4 mmol) in a portion and resulting reaction mixture was stirred for 1 h at 25° C. The reaction mixture was basified with aqueous NaOH and extracted with EtOAc. Combined organic layers were dried over Na₂SO₄ and concentrated in vacuo, yielding an oil (0.47 g, 3.2 mmol, 96%) which was identified as the amine (>95%) and subjected to the following reaction without further purification.

6-(2-Imidazolin-2-ylamino)benzothiazole

A solution of the amine (0.32 g, 2.1 mmol) and ISA (0.55 g, 4.1 mmol) in 10 mL of isobutanol was stirred at reflux for 12 h. The reaction mixture was concentrated in vacuo, yielding oily residue which was purified on column chromatography (20% NH₃ saturated MeOH/EtOAc) to provide 0.31 g (1.4 mmol, 64%) of the desired product. The product obtained was converted to the fumarate salt and recrystallized from MeOH to provide 0.26 g of the product as a white solid: mp 215°–216° C.; ¹H NMR (CD₃OD) δ9.26 (s, 1H), 8.09 (d, J=5.8 Hz, 1H), 8.01 (d, J=2.0 Hz, 1H), 7.42 (dd, J=2.0, 5.8 Hz, 1H), 3.75 (s, 4H); Anal. Calc. for C₁₀H₁₀N₄S.1.0C₄H₄O₄ requires C, 50.29; H, 4.22; N, 16.76. Found: C, 50.35; H, 4.31; N, 16.68.

EXAMPLE 15

6-(2-Thiazolin-2-ylamino)benzothiazole

To a solution of 6-aminobenzothiazole (0.15 g, 1.0 mmol) in 10 mL of CHCl₃ and 10 mL of saturated aqueous NaHCO₃ was added thiophosgene (0.20 mL, 2.6 mmol) in a portion. The reaction mixture was stirred for 1 h at 25° C. Organic layer was separated from aqueous layer. Aqueous layer was then extracted with EtOAc several times. Combined organic extracts were dried over Na₂SO₄ and concentrated in vacuo, providing an oil which was dissolved in 10 mL of THF with of triethylamine (1 mL) and chloroethylamine.HCl (0.5 g). Resulting solution was stirred for 12 h at reflux. It was concentrated in vacuo to yield oily residue which was purified on column chromatography (5% NH₃ saturated MeOH/EtOAc) to provide 0.16 g (0.68 mmol, 68%) of the desired product. The product obtained was converted to the fumarate salt and recrystallized from MeOH to provide 0.18 g of the product as a white crystal: mp 181°–183° C.; ¹H NMR (CD₃OD) δ9.11 (s, 1H), 8.02 (d, J=2.0 Hz, 1H), 7.96 (d, J=5.8 Hz, 1H), 7.32 (dd, J=2.0, 5.8 Hz, 1H), 3.90 (t, J=4.8 Hz, 2H), 3.39 (t, J=4.8 Hz, 2H); Anal. Calc. for C₁₀H₉N₃S₂.1.0C₄H₄O₄ requires C, 47.85; H, 3.73; N, 11.96. Found: C, 48.86; H, 3.86; N, 12.15.

EXAMPLE 16

7-Methyl-6-(2-imidazolin-2-ylamino)benzothiazole

7-Methyl-6-nitrobenzothiazole

To a solution of 6-nitrobenzothiazole (1.4 g, 7.7 mmol) in 50 mL of THF was added 5.1 mL of MeMgBr (15.3 mmol) dropwise in 0.5 h period at 0° C. The reaction mixture was then stirred for additional 2 h. It was quenched by adding THF solution of 2,3-dichloro-5,6-dicyanobenzoquinone until the color of the solution turns to dark green. The reaction mixture was concentrated in vacuo to yield a dark solid which was subjected to column chromatography (CHCl₃, neat) to provide 0.68 g (3.5 mmol, 46%) of the desired product.

7-Methyl-6-aminobenzothiazole

To a solution of SnCl₂ (3.0 g, 3.8 mmol) and 10 mL of con.HCl was added 7-methyl-6-nitrobenzothiazole (0.68 g, 3.5 mmol) in a portion and the resulting reaction mixture was stirred for 1 h at 25° C. The reaction mixture was basified with aqueous NaOH and extracted with EtOAc and CHCl₃. Combined organic layers were dried over Na₂SO₄ and concentrated in vacuo, yielding an oil (0.65 g, >95%) which was identified as the desired amine and subjected to a following reaction without further purification.

7-Methyl-6-(2-imidazolin-2-ylamino)benzothiazole.

A solution of the amine (0.32 g, 2.1 mmol) and ISA (0.80 g, 5.4 mmol) in 10 mL of isobutanol was stirred at reflux for 12 h. The reaction mixture was concentrated in vacuo, yielding oily residue which was purified on column chromatography (30% NH₃ saturated MeOH/EtOAc) to provide 0.31 g (1.3 mmol, 64%) of the desired product. The product obtained was converted to the fumarate salt and recrystallized from EtOH to provide 0.31 g of the product as a white solid: mp 213°–215° C.; ¹H NMR (CD₃OD) δ9.31 (s, 1H), 7.96 (d, J=5.8 Hz, 1H), 7.43 (d, J=5.8 Hz, 1H), 3.75 (s, 4H); Anal. Calc. for C₁₁H₁₂N₄S.1.0C₄H₄O₄ requires C, 51.75; H, 4.63; N, 16.08. Found: C, 51.52; H, 4.75; N, 15.90.

EXAMPLE 17

7-Bromo-5-(2-imidazolin-2-ylamino)benzothiazole

7-Bromo-6-aminobenzothiazole

To a solution of 6-aminobenzothiazole (16 g, 107 mmol) in 100 mL of AcOH was added Br₂ (2.0 mL, 43 mmol) dropwise and the resulting reaction mixture was stirred for 1 h at 25° C. Reaction mixture was concentrated in vacuo, yielding a yellow solid which was dissolved in EtOAc and washed with aq. NaHCO₃. Organic layer was dried over Na₂SO₄ and concentrated in vacuo, yielding an oil which was subjected to column chromatography (10–50% EtOAc/n-Hexane) to obtain 7.8 g (34 mmol, 80%) of the desired product.

5-Nitro-6-amino-7-bromobenzothiazole

A solution of the amine (1.9 g, 8.2 mmol) in 5 mL of 1:1 mixture of HNO₃ and H₂SO₄ was stirred for 12 h at −30° C. The reaction mixture was dissolved in 50 mL of H₂O and extracted with EtOAc several times. Organic extracts were washed with aq. NaHCO₃, dried over Na₂SO₄ and concentrated in vacuo, yielding an oil (2.3 g, >95%) which, in NMR analysis, corresponds to the expected product and subjected to the following reaction without further purification.

5-Nitro-7-bromobenzothiazole

To a solution of 5-nitro-6-amino-7-bromobenzothiazole (1.0 g, 3.7 mmol) in 4 mL of sulfuric acid was added nitrososulfuric acid (1.2 g, 9.5 mmol) in a portion. The resulting reaction mixture was stirred for 12 h at 25° C. The reaction mixture was then cooled to 0° C. and 1 mL of H₃PO₂ was added into the solution. It was stirred for 12 h at another 25° C. and for 2 h at 50° C. The reaction mixture was then poured into EtOAc and washed with aq. NaHCO₃. Organic layer was dried over Na₂SO₄ and concentrated in vacuo to provide an oil (0.85 g, 3.2 mmol, 89%), which was characterized as the desired product (>95% pure) and subjected to a following reaction without further purification.

5-Amino-7-bromobenzothiazole

To a solution of SnCl$_2$.2H$_2$O (0.5 g, 2.2 mmol) in 5 mL of HCl was added 5-nitro-7-bromobenzothiazole (82 mg, 0.32 mmol) in a portion and the resulting reaction mixture was stirred for 1 h at 25° C. The reaction mixture was basified with aq. NaOH and extracted with EtOAc. Organic extracts were dried over Na$_2$SO$_4$ and concentrated in vacuo to yield 70 mg (31 mmol, 96%) of the desired product.
7-Bromo-5-(2-imidazolin-2-ylamino)benzothiazole A solution of the amine (0.13 g, 0.57 mmol) and ISA (0.45 g, 3.3 mmol) in 10 mL of isobutanol was stirred at reflux for 12 h. The reaction mixture was concentrated in vacuo, yielding an oil, which was subjected to column chromatography (30% NH$_3$ saturated MeOH/EtOAc) to yield 70 mg (2.4 mmol, 43%) of the desired product. The product obtained was converted to the fumarate salt and recrystallized from MeOH to provide 43 mg of the product as a white solid: mp 209°–211° C.; $^1$H NMR (CD$_3$OD) δ9.35 (s, 1H), 7.85 (d, J=1.8 Hz, 1H), 7.45 (d, J=1.8 Hz, 1H), 3.71 (s, 4H); Anal. Calc. for C$_{10}$H$_9$N$_4$BrS.1.0C$_4$H$_4$O$_4$ requires C, 40.69; H, 3.17; N, 13.56. Found: C, 40.56; H, 3.11; N, 13.86.

EXAMPLE 18

7-Chloro-5-(2-imidazolin-2-ylamino)benzothiazole

7-Chloro-6-aminobenzothiazole

To a solution of 6-aminobenzothiazole (2.0 g, 13.4 mmol) in 100 mL of AcOH was added a solution of Cl$_2$ saturated AcOH and the resulting reaction mixture was stirred for 1 h at 25° C. Reaction mixture was concentrated in vacuo, yielding a yellow solid which was dissolved in EtOAc and washed with aq. NaHCO$_3$. Organic layer was dried over Na$_2$SO$_4$ and concentrated in vacuo, yielding an oil which was subjected to column chromatography (10–50% EtOAc/n-Hexane) to obtain 7.8 g (34 mmol, 80%) of the desired product.

5-Nitro-6-amino-7-chlorobenzothiazole

A solution of the amine (1.1 g, 6.0 mmol) in 5 mL of 1:1 mixture of HNO$_3$ and H$_2$SO$_4$ was stirred for 12 h at −30° C. The reaction mixture was dissolved in 50 mL of H$_2$O and extracted with EtOAc several times. The organic extracts were washed with aq. NaHCO$_3$, dried over Na$_2$SO$_4$ and concentrated in vacuo, yielding an oil (0.21 g, 0.91 mmol, 16%) which, in NMR analysis, corresponds to the expected product and subjected to the following reaction without further purification.

5-Nitro-7-chlorobenzothiazole

To a solution of 5-nitro-6-amino-7-chlorobenzothiazole (0.21 g, 0.91 mmol) in 4 mL of sulfuric acid was added nitrososulfuric acid (0.20 g, 1.6 mmol) in a portion. The resulting reaction mixture was stirred for 12 h at 25° C. It was then cooled to 0° C. and 0.3 mL of H$_3$PO$_2$ was added into the mixture. Reaction mixture was stirred for another 12 h at 25° C. and for 2 h at 50° C., poured into EtOAc and washed with aq. NaHCO$_3$. Organic layer was dried over Na$_2$SO$_4$ and concentrated in vacuo to provide an oil, which was purified on column chromatography (EtOAc, neat) to produce the desired product (0.12 g, 0.56 mmol, 62%).

5-Amino-7-chlorobenzothiazole

To a solution of SnCl$_2$.2H$_2$O (0.5 g, 2.2 mmol) in 5 mL of HCl was added 5-nitro-7-chlorobenzothiazole (0.12 mg, 0.56 mmol) in a portion and the resulting reaction mixture was stirred for 1 h at 25° C. The reaction mixture was basified with aq. NaOH and extracted with EtOAc. Organic extracts were dried over Na$_2$SO$_4$ and concentrated in vacuo to yield 110 mg (0.54 mmol, >95%) of the desired product.

7-Chloro-5-(2-imidazolin-2-ylamino)benzothiazole

A solution of the amine (0.10 g, 0.54 mmol) and ISA (0.45 g, 3.3 mmol) in 10 mL of isobutanol was stirred at reflux for 12 h. The reaction mixture was concentrated in vacuo, yielding an oil, which was subjected to column chromatography (30% NH$_3$ saturated MeOH/EtOAc) to yield 70 mg (0.27 mmol, 52%) of the desired product. The product obtained was converted to the fumarate salt and recrystallized from isopropanol to provide 21 mg of the product as a white solid: mp 203°–205° C.; $^1$H NMR (CD$_3$OD) δ9.35 (s, 1H), 7.85 (d, J=1.8 Hz, 1H), 7.45 (d, J=1.8 Hz, 1H), 3.71 (s, 4H); Anal. Calc. for C$_{10}$H$_9$N$_4$ClS.1.0C$_4$H$_4$O$_4$ requires C, 45.60; H, 3.55; N, 15.19. Found: C, 44.76; H 3.67; N, 14.91.

EXAMPLE 19

7-Methyl-5-(2-imidazolin-2-ylamino)benzothiazole

7-Methyl-5-nitrobenzothiazole

A solution of 7-bromo-5-nitrobenzothiazole (0.15 g, 0.58 mmol), tetramethyltin (0.20 mL, 0.1.5 mmol) and catalytic amount of Cl$_2$Pd(PPh$_3$)$_2$ in a sealed tube was stirred for 12 h at 90° C. The reaction mixture was diluted with EtOAc and washed with brine several times. Organic solution was dried over Na$_2$SO$_4$ and concentrated in vacuo, yielding an oil which was subjected to column chromatography (EtOAc, neat) to provide 65 mg (0.32 mmol, 67%) of the desired product.

7-Methyl-5-aminobenzothiazole

To a solution of SnCl$_2$ (1.5 g, 1.9 mmol) in 5.0 mL of HCl was added 7-methyl-5-nitrobenzothiazole (65 m g, 0.32 mmol) in a portion and resulting reaction mixture was stirred for 1 h at 25° C. The reaction mixture was basified with aqueous NaOH and extracted with EtOAc and CHCl$_3$. Combined organic layers were dried over Na$_2$SO$_4$ and concentrated in vacuo, yielding an oil (0.30 g, >95%) which was identified as the desired amine (>95% pure) and subjected to the following reaction without further purification.
7-Methyl-5-(2-imidazolin-2-ylamino)benzothiazole.

A solution of the amine (0.12 g, 0.73 mmol) and ISA (0.35 g, 2.6 mmol) in 5 mL of isobutanol was stirred at reflux for 12 h. The reaction mixture was concentrated in vacuo, yielding oily residue which was purified on column chromatography (30% NH$_3$ saturated MeOH/EtOAc) to provide 0.16 g (0.69 mmol, 95%) of the desired product. The product obtained was converted to the fumarate salt and recrystallized from isopropanol to provide 15 mg of the product as a white solid: mp 179°–181° C.; $^1$H NMR (CD$_3$OD) δ9.35 (s, 1H), 7.90 (d, J=1.8 Hz, 1H),7.23 (d, J=1.8 Hz, 1H), 3.77 (s, 4H), 2.59 (s, 3H); Anal. Calc. for C$_{11}$H$_{12}$N$_4$S.1.0C$_4$H$_4$O$_4$ requires C, 51.72; H, 4.63; N, 16.08. Found: C, 51.46; H, 4.58; N, 15.98.

EXAMPLE 20

7-Ethyl-5-(2-imidazolin-2-ylamino)benzothiazole

7-Ethyl-5-nitrobenzothiazole

A solution of 7-bromo-5-nitrobenzothiazole (0.15 g, 0.58 mmol), tetraethyltin (0.18 mL, 0.87 mmol) and catalytic amount of Cl$_2$Pd(PPh$_3$)$_2$ in a sealed tube was stirred for 12 h at 90° C. The reaction mixture was diluted with EtOAc and washed with brine several times. Organic solution was dried over Na$_2$SO$_4$ and concentrated in vacuo, yielding an oil which was subjected to column chromatography (EtOAc, neat) to provide 91 mg (0.44 mmol, 75%) of the desired product.

7-Ethyl-5-aminobenzothiazole

To a solution of SnCl$_2$ (1.5 g, 1.9 mmol) and 5.0 mL of HCl was added 7-ethyl-5-nitrobenzothiazole (0.12 g, 0.57 mmol) in a portion and resulting reaction mixture was stirred for 1 h at 25° C. The reaction mixture was basified with aqueous NaOH and extracted with EtOAc and $CHCl_3$. Combined organic layers were dried over $Na_2SO_4$ and concentrated in vacuo, yielding an oil (0.10 g, >95%) which was identified as the desired amine (>95% pure) and subjected to a following reaction without further purification. 7-Ethyl-5-(2-imidazolin-2-ylamino)benzothiazole.

A solution of the amine (0.10 g, 0.56 mmol) and ISA (0.20 g, 1.4 mmol) in 5 mL of isobutanol was stirred at reflux for 12 h. The reaction mixture was concentrated in vacuo, yielding oily residue which was purified on column chromatography (30% $NH_3$ saturated MeOH/EtOAc) to provide 69 mg (0.28 mmol, 50%) of the desired product. The product obtained was converted to the fumarate salt and recrystallized from isopropanol to provide 25 mg of the product as a white solid: mp 218°–220° C.; $^1H$ NMR ($CD_3OD$) $\delta 9.35$ (s, 1H), 7.91 (d, J=1.8 Hz, 1H), 7.23 (d, J=1.8 Hz, 1H), 3.77 (s, 4H), 2.32 (q, 2H), 1.25 (t, 3H); Anal. Calc. for $C_{12}H_{14}N_4S.1.0C_4H_4O_4$ requires C, 53.03; H, 5.01; N, 15.46. Found: C, 52.86; H, 5.63; N, 15.55.

EXAMPLE 21

Protocol for the determination of the potency of $\alpha_2$ agonists

The activity of the compounds at the different receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

Human $\alpha_{2A}$ Adrenergic Receptor: The entire coding region of $\alpha_{2A}$ (1350 bp), including 1.0 kilobasepairs of 5' untranslated sequence (5'UT) and 100 bp of 3' untranslated sequence (3'UT), was cloned into the SmaI site of the eukaryotic expression vector pcEXV-3. The insert housing this coding region was an approximately 2.5 kb KpnI/HindIII human placenta genomic fragment which was end-blunted by either $T_4$ polymerase or Klenow fragment of DNA polymerase. Stable cell lines were obtained by cotransfection with the Plasmid pcEXV-3 plasmid containing the $\alpha_{2A}$ receptor gene and the plasmid pGCcos3neo (which contains the aminoglycoside transferase gene) into LM(tk$^-$) cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 µg/ml streptomycin sulfate. Stable clones were then selected for resistance to the antibiotic G-418 (1 mg/mL), and membranes were harvested and assayed for their ability to bind [$^3H$] rauwolscine as described below (see "Radioligand Binding Assays")

Human $\alpha_{2B}$ Adrenergic Receptor: The entire coding region of $\alpha_{2B}$ (1350 bp), including 393 bp of 5' untranslated sequence and 11 bp of 3' untranslated sequence, was cloned into the eukaryotic expression vector pcEXV-3. Stable cell lines were produced and selected as described above, except that a Y1 cell was used as host instead of an LM(tk–) cell.

Human $\alpha_{2C}$ Adrenergic Receptor: The entire coding region of $\alpha_{2C}$ (1383 bp), including 2 bp of 5' UT and 400 bp of 3' UT, was cloned into the SmaI site of the eukaryotic expression vector pCEXV-3. The insert housing this coding region was an @ 1.8 kb NcoI/EcoRI human spleen genomic fragment which was end-blunted by either $T_4$ polymerase or Klenow fragment of DNA polymerase. Stable cell lines were produced and selected as described above.

Human Alpha-1 Adrenergic Receptor Nomenclature: The cloned human alpha-1 adrenergic receptor subtypes referred to throughout this application as $\alpha_{1A}$, $\alpha_{1B}$, and $\alpha_{1C}$ have recently been assigned new subtype designations by the IUPHAR Nomenclature Committee as outlined in the 1995 Receptor and Ion Channel Nomenclature Supplement (Watson and Girdlestone, 1995). In the new nomenclature system the cloned human $\alpha_{1A}$ receptor referred to herein was given the appellation "$\alpha_{1D}$," while the cloned human $\alpha_{1C}$ receptor referred to herein was given the appellation "$\alpha_{1A}$". However, throughout this application and the supporting tables and figures the old nomenclature will be used to describe the cloned human alpha-1 adrenergic receptor subtypes. The old nomenclature is used throughout this application because stable cell lines expressing the cloned human alpha-1 adrenergic receptors were produced and deposited with the ATCC according to the Budapest Treaty for the Deposit of Microorganisms, under designations assigned before the nomenclature change.

Human $\alpha_{1A}$ Adrenergic Receptor: The entire coding region of $\alpha_{1A}$ (1719 bp), including 150 bp of 5' untranslated sequence (5'UT) and 300 bp of 3' untranslated sequence (3'UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequences were contained on a 1.2 kb SmaI-XhoI genomic fragment (the vector-derived BamHI site was used for subcloning instead of the internal insert-derived SmaI site) and 3' sequences were contained on 1.3 kb XhoI-ClaI cDNA fragment (the ClaI site was from the vector polylinker). Stable cell lines were produced and selected as described above.

Human $\alpha_{1B}$ Adrenergic Receptor: The entire coding region of $\alpha_{1B}$ (1563 bp), including 200 basepairs and 5' untranslated sequence (3'UT) and 600 bp of 3' untranslated sequence (3'UT), was cloned into the EcoRI site of pCEXV-3 eukaryotic expression vector. The construct involved ligating the full-length containing EcoRI brainstem cDNA fragment from λ ZapII into the expression vector. Stable cell lines were produced and selected as described above.

Human $\alpha_{1C}$ Adrenergic Receptor: The entire coding region of $\alpha_{1C}$ (1401 bp), including 400 basepairs of 5' untranslated sequence (5'UT) and 200 p of 3' untranslated sequences (3'UT), was cloned into the KpnI site of the polylinker-modified pCEXV-3-derived eukaryotic expression vector, EXJ.RH. The construct involved ligation three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII nad PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were produced and selected as described above.

Cell line deposits: In connection with this invention, stable cell lines expressing the cloned human adrenergic receptors described above have been deposited pursuant to, and in satisfaction of, the Budapest Treaty on the Deposit of Microorganisms for the Purpose of Patent Procedure, with the American Type Culture Collection ("ATCC"), 12301 Parklawn Drive, Rockville, Md., 0852, as follows in Table 1:

TABLE 1

ATCC Deposits

| Receptor | Designation | ATCC Accession No. | Deposit Date |
|---|---|---|---|
| human $\alpha_{1A}$ | L-$\alpha_{1A}$ | CRL 11138 | September 25, 1992 |
| human $\alpha_{1B}$ | L-$\alpha_{1B}$ | CRL 11139 | September 25, 1992 |
| human $\alpha_{1C}$ | L-$\alpha_{1C}$ | CRL 11140 | September 25, 1992 |
| human $\alpha_{2A}$ | L-$\alpha_{2A}$ | CRL 11180 | November 6, 1992 |
| human $\alpha_{2B}$ | Y-a2B-2 | CRL 11888 | May 11, 1995 |
| human $\alpha_{2C}$ | L-$\alpha_{2C}$ | CRL 11181 | November 6, 1992 |

Radioligand Binding Assays: Transfected cells from culture flasks were scraped into 5 mL of 5 mM Tris-HCl, 5 mM EDTA, pH 7.5, and lysed by sonication. The cell lysates were centrifuged at 1000 rpm for 5 min at 4° C., and the supernatant was centrifuged at 30,000× g for 20 min at 4° C. The pellet was suspended in 50 mM Tris-HCl, 1 mM MgCl$_2$, and 0.1% Ascorbic acid at pH 7.5. Binding of $\alpha_2$ antagonist [$^3$H] rauwolscine (0.5 mM) to membrane preparations of LM(tk−) cells was done in a final volume of 0.25 mL and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

Measurement of Agonist Activity: The agonist activity (expressed as pEC$_{50}$) was measured as a function of the ability to inhibit the forskolin-stimulated synthesis of cyclic adenosine monophosphate (cAMP). The stably transfected cells were incubated in Ham's F10 with 5 mM theophylline, 10 mM HEPES, 10 μM pargyline, and/or appropriate concentrations of forskolin for 20 min at 37° C. in 5% CO$_2$. The tested compounds were then added to a final concentration of 0.001 nM to 1 μM and incubated for an additional 15 min at 37° C. in 5% CO$_2$. The medium was aspirated and the reaction was stopped by the addition of 100 mM HCl. To demonstrate competitive antagonism, a dose-response curve for norepinephrine was measured in parallel, using a fixed dose of norepinephrine (0.32 μM). Intrinsic activity is the measure of maximum activity induced by a compound relative to the maximum activity induced by norepinephrine. The assessment of cAMP formation is determined by radioimmunoassay (cAMP radioimmunoassay kit; Advanced Magnetics, Cambridge, Mass.). Radioactivity was quantified using a Packard COBRA Auto Gamma counter, equipped with data reduction software.

Results: The results of the pharmacological evaluations of the compounds of the present invention are summarized in Table 2, I.A.=Intrinsic Activity; N.A.=Inactive at concentrations up to 100 μM.

TABLE 2

Pharmacologic Evaluation

| Example | | Alpha-2 | | | Alpha-1 | | |
|---|---|---|---|---|---|---|---|
| | | A | B | C | A | B | C |
| 2 | pKi | 9.14 | 8.54 | 7.89 | 8.54 | 7.57 | 7.72 |
| | pEC50 | 9.36 | 8.72 | 9.39 | | | |
| | I.A | 0.46 | 0.75 | 1.00 | | | |
| 5 | pKi | 8.13 | 7.81 | 7.36 | 6.79 | 4.90 | 5.84 |
| | pEC50 | N.A | 6.50 | 9.23 | | | |
| | I.A | | 0.60 | 1.00 | | | |
| 6 | pKi | 8.31 | 7.34 | 6.93 | 7.03 | 7.25 | 6.73 |
| | pEC50 | N.A | 7.09 | 7.39 | | | |
| | I.A | | 0.70 | 0.90 | | | |
| 8 | pKi | 9.08 | 8.31 | 7.62 | | | |
| | pEC50 | 7.86 | 7.35 | 8.66 | | | |
| | I.A | 0.60 | 0.80 | 1.00 | | | |
| 13 | pKi | 8.43 | 8.34 | 7.69 | 6.73 | 6.15 | 6.15 |
| | pEC50 | 7.91 | 7.99 | 9.22 | | | |
| | I.A | 0.98 | 0.82 | 1.00 | | | |
| 14 | pKi | 8.07 | 7.85 | 6.99 | 5.77 | 5.44 | 5.63 |
| | pEC50 | 6.38 | 7.85 | 8.26 | | | |
| | I.A | 0.51 | 0.47 | 1.00 | | | |
| 15 | pKi | 6.94 | 6.79 | 5.97 | 5.22 | 5.14 | 5.24 |
| | pEC50 | 5.51 | 6.86 | 7.77 | | | |
| | I.A | 0.58 | 0.57 | 0.88 | | | |

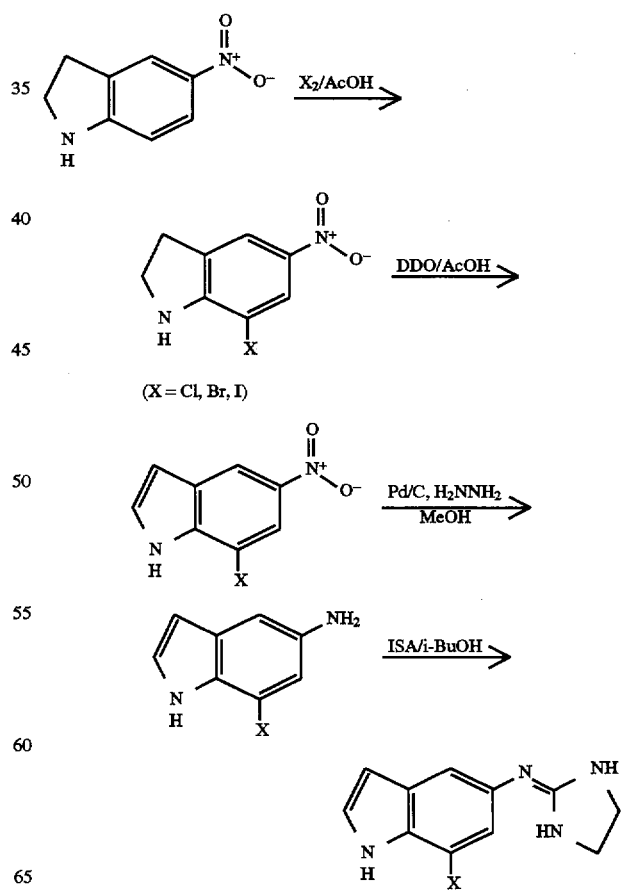

Scheme 1
illustrates schematically the synthesis of
7-substituted derivatives of 5-(2-imidazolin-2ylamino) indole.

-continued
Scheme 1
illustrates schematically the synthesis of
7-substituted derivatives of 5-(2-imidazolin-2ylamino) indole.
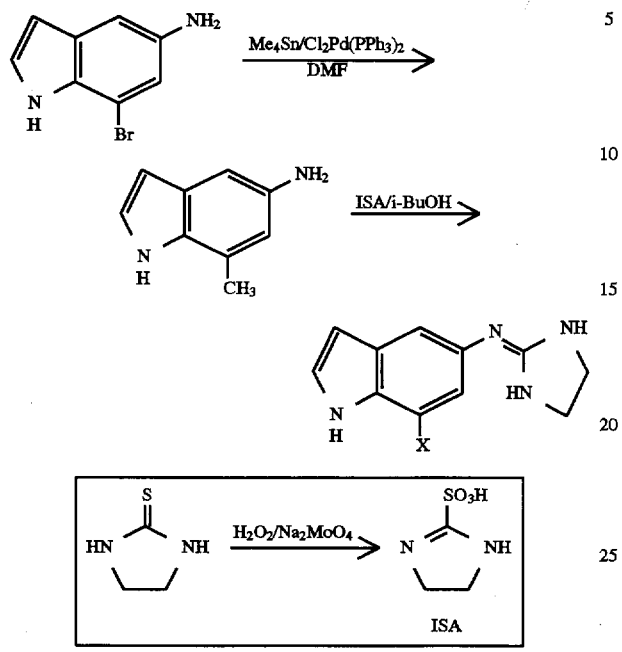
Scheme 2 illustrates schematically the synthesis of 7-substituted derivatives of 5-(2-imidazolin-2ylamino) indole.
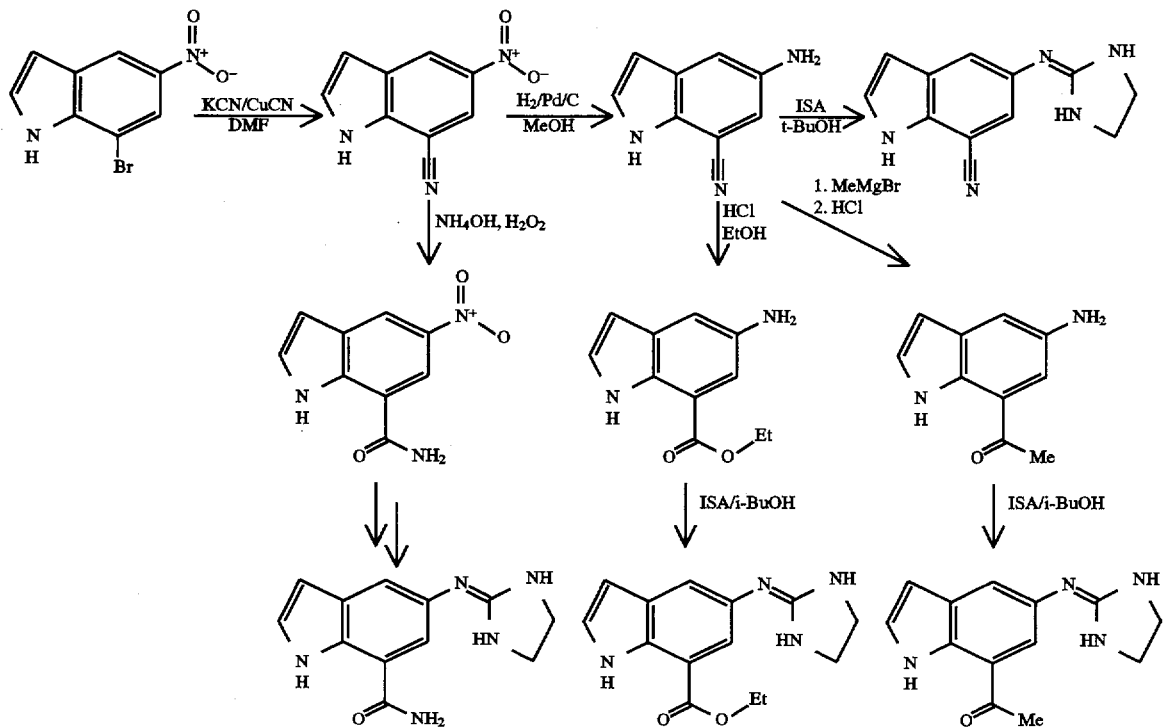

Scheme 3 illustrates schematically the synthesis of 7-substituted branched alkyl/alkenyl derivatives of 5-(2-imidazolin-2ylamino) indole where R, $R_1$ and $R_2$ are alkyl or alkenyl groups.

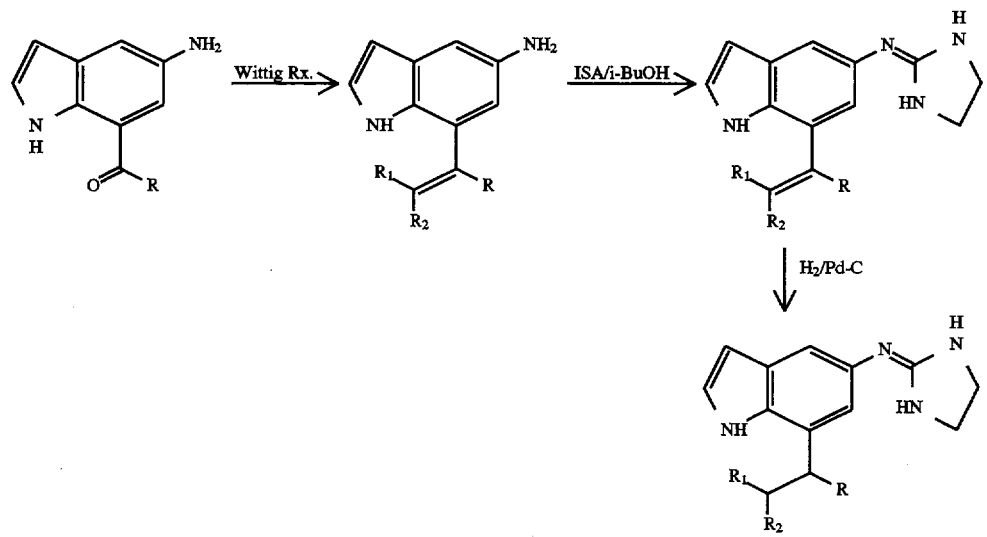

Scheme 4 illustrates schematically the synthesis of a 5-(2-imidazolin-2ylamino) benzothiazole as well as synthesis of 7-substituted derivatives of 6-(2-imidazolin-2ylamino) benzothiazole, where R is alkyl or alkenyl.

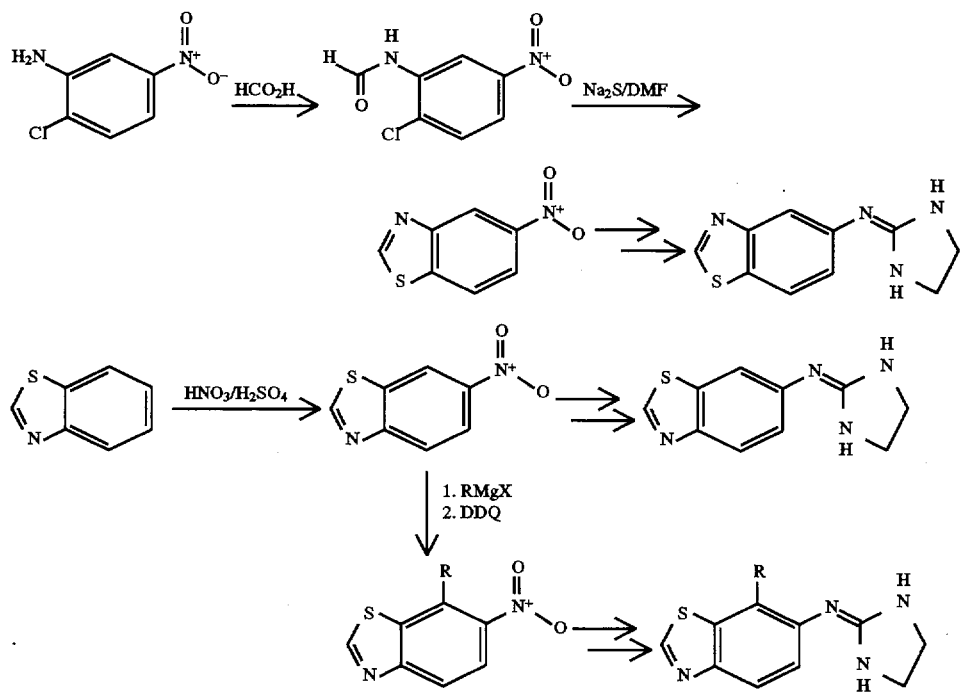

Scheme 5 illustrates schematically the synthesis of 7-substituted derivatives of 5-(2-imidazolin-2ylamino) benzothiazole, where R is alkyl or alkenyl.

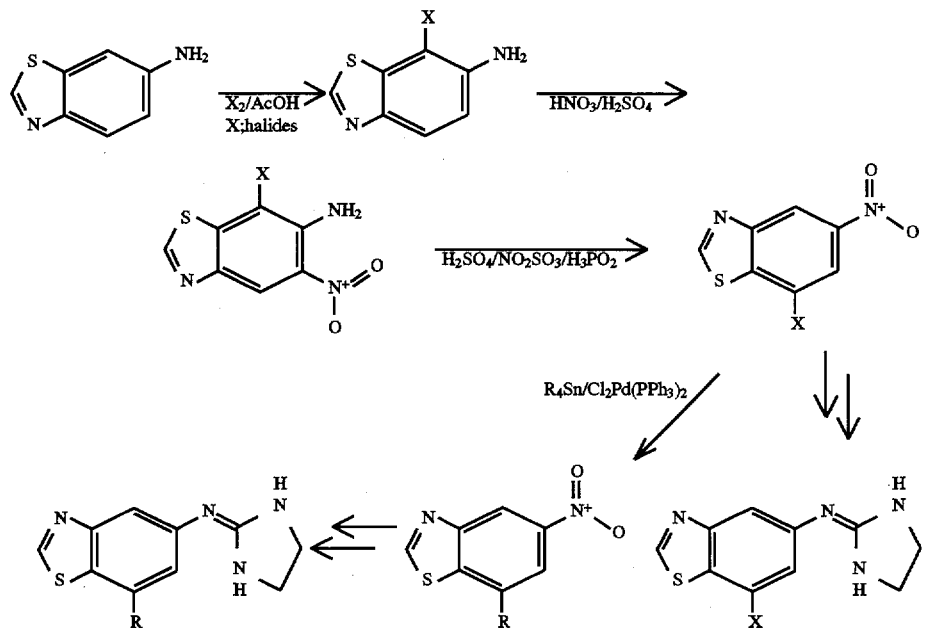

Scheme 6 illustrates schematically the synthesis of a 6-(2-thiazolin-2ylamino) benzothiazole.

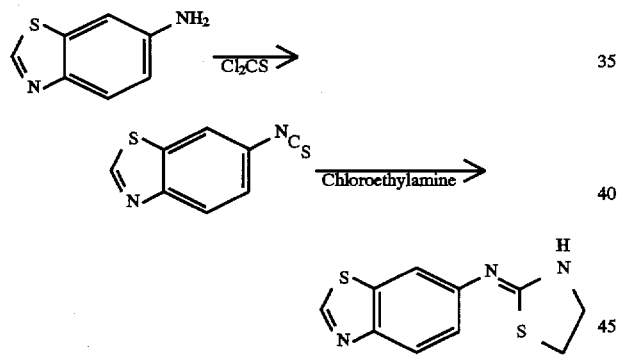

What is claimed is:

1. A compound having the structure:

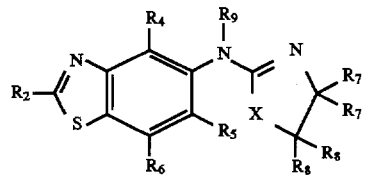

wherein $R_2$ is —H; straight chained or branched $C_1$–$C_7$ alkyl, monofluoroalkyl or polyfluoroalkyl; straight chained or branched $C_2$–$C_7$ alkenyl or alkynyl;

wherein each of $R_4$, $R_5$ and $R_6$ is independently —H, —F, —Cl, —Br, —I, —OH, —OR$_7$, —OCOR$_7$, —SR$_7$, —N(R$_7$)$_2$, —CN, —CO$_2$R$_7$, —CON(R$_7$)$_2$, or —COR$_7$; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl or cycloalkenyl; $C_4$–$C_7$ heterocycloalkyl or heteroaryl; phenyl, substituted phenyl or phenyl substituted $C_1$–$C_4$ alkyl wherein the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

wherein each $R_7$ is independently —H; —N(R$_{10}$)$_2$, —NR$_{10}$COR$_{10}$, —(CH$_2$)$_n$OR$_{10}$, —SO$_n$R$_{10}$, —SO$_n$N(R$_{10}$)$_2$, —(CH$_2$)$_n$N(R$_{10}$)$_2$, or —(CH$_2$)$_n$NR$_{10}$COR$_{10}$; straight chained or branched $C_1$–$C_7$ alkyl; straight chained or branched $C_2$–$C_7$ alkenyl or alkynyl; phenyl, substituted phenyl or phenyl substituted $C_1$–$C_4$ alkyl wherein the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

wherein each n is independently an integer from 1 to 4;

wherein each $R_8$ is independently —H; straight chained or branched $C_1$–$C_7$ alkyl; straight chained or branched $C_2$–$C_7$ alkenyl or alkynyl; $C_3$–$C_7$ cycloalkyl or cycloalkenyl; phenyl, substituted phenyl or phenyl substituted $C_1$–$C_4$ alkyl wherein the substituted phenyl or phenyl substituted $C_1$–$C_4$ alkyl is substituted with —H, —F, —Cl, —Br, —I, —NO$_2$, —CN, straight chained or branched $C_1$–$C_7$ alkyl, straight chained or branched $C_2$–$C_7$ alkenyl or alkynyl, —NR$_{10}$, —OR$_{10}$, —COR$_{10}$, —CO$_2$R$_{10}$, or —CON(R$_{10}$)$_2$;

wherein $R_9$ is independently —H; straight chained or branched $C_1$–$C_7$ alkyl; straight chained or branched $C_2$–$C_7$ alkenyl or alkynyl; $C_3$–$C_7$ cycloalkyl or cycloalkenyl; $C_4$–$C_7$ heterocycloalkyl or heteroaryl; phenyl, substituted phenyl or phenyl substituted $C_1$–$C_4$ alkyl wherein the substituted phenyl or phenyl substituted $C_1$–$C_4$ alkyl is substituted with —H, —F, —Cl, —Br, —I, —NO$_2$, —CN, straight chained or branched C$_1$–C$_7$ alkyl, straight chained or branched C$_2$–C$_7$ alkenyl or alkynyl, —NR$_{10}$, —OR$_{10}$, —COR$_{10}$, —CO$_2$R$_{10}$, or —CON(R$_{10}$)$_2$; —wherein each R$_{10}$ is independently —H; straight chained or branched C$_1$–C$_7$ alkyl; straight chained or branched C$_2$–C$_7$ alkenyl or alkynyl; and wherein X is independently CH$_2$, O, NH or S; or a pharmaceutically acceptable salt thereof.

2. An (−) enantiomer of the compound of claim 1.
3. An (+) enantiomer of the compound of claim 1.
4. A compound having the structure:

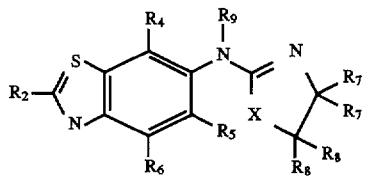

wherein R$_2$ is —H; straight chained or branched C$_1$–C$_7$ alkyl, monofluoroalkyl or polyfluoroalkyl; straight chained or branched C$_2$–C$_7$ alkenyl or alkynyl;

wherein each of R$_4$, R$_5$ and R$_6$ is independently —H, —F, —Cl, —Br, —I, —OH, —OR$_7$, —OCOR$_7$, —SR$_7$, —N(R$_7$)$_2$, —CN, —CO$_2$R$_7$, —CON(R$_7$)$_2$, or —COR$_7$; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl or cycloalkenyl; C$_4$–C$_7$ heterocycloalkyl or heteroaryl; phenyl, substituted phenyl or phenyl substituted C$_1$–C$_4$ alkyl wherein the substituted phenyl or phenyl substituted C$_1$–C$_4$ alkyl is substituted with —H, —F, —Cl, —Br, —I, —NO$_2$, —CN, straight chained or branched C$_1$–C$_7$ alkyl, straight chained or branched C$_2$–C$_7$ alkenyl or alkynyl, —NR$_{10}$, —OR$_{10}$, —COR$_{10}$, —CO$_2$R$_{10}$, or —CON(R$_{10}$)$_2$;

wherein each R$_7$ is independently —H; —N(R$_{10}$)$_2$, —NR$_{10}$COR$_{10}$, —(CH$_2$)$_n$OR$_{10}$, —SO$_n$R$_{10}$, —SO$_n$N(R$_{10}$)$_2$, —(CH$_2$)$_n$N(R$_{10}$)$_2$, or —(CH$_2$)$_n$NR$_{10}$COR$_{10}$; straight chained or branched C$_1$–C$_7$ alkyl; straight chained or branched C$_2$–C$_7$ alkenyl or alkynyl; phenyl, substituted phenyl or phenyl substituted C$_1$–C$_4$ alkyl wherein the substituted phenyl or phenyl substituted C$_1$–C$_4$ alkyl is substituted with —H, —F, —Cl, —Br, —I, —NO$_2$, —CN, straight chained or branched C$_1$–C$_7$ alkyl, straight chained or branched C$_2$–C$_7$ alkenyl or alkynyl, —NR$_{10}$, —OR$_{10}$, —COR$_{10}$, —CO$_2$R$_{10}$, or —CON(R$_{10}$)$_2$;

wherein each n is independently an integer from 1 to 4;

wherein each R$_8$ is independently —H; straight chained or branched C$_1$–C$_7$ alkyl; straight chained or branched C$_2$–C$_7$ alkenyl or alkynyl; C$_3$–C$_7$ cycloalkyl or cycloalkenyl; phenyl, substituted phenyl or phenyl substituted C$_1$–C$_4$ alkyl wherein the substituted phenyl or phenyl substituted C$_1$–C$_4$ alkyl is substituted with —H, —F, —Cl, —Br, —I, —NO$_2$, —CN, straight chained or branched C$_1$–C$_7$ alkyl, straight chained or branched C$_2$–C$_7$ alkenyl or alkynyl, —NR$_{10}$, —OR$_{10}$, —COR$_{10}$, —CO$_2$R$_{10}$, or —CON(R$_{10}$)$_2$;

wherein R$_9$ is independently —H; straight chained or branched C$_1$–C$_7$ alkyl; straight chained or branched C$_2$–C$_7$ alkenyl or alkynyl; C$_3$–C$_7$ cycloalkyl or cycloalkenyl; C$_4$–C$_7$ heterocycloalkyl or heteroaryl; phenyl, substituted phenyl or phenyl substituted C$_1$–C$_4$ alkyl wherein the substituted phenyl or phenyl substituted C$_1$–C$_4$ alkyl is substituted with —H, —F, —Cl, —Br, —I, —NO$_2$, —CN, straight chained or branched C$_1$–C$_7$ alkyl, straight chained or branched C$_2$–C$_7$ alkenyl or alkynyl, —NR$_{10}$, —OR$_{10}$, —COR$_{10}$, —CO$_2$R$_{10}$, or —CON(R$_{10}$)$_2$;

wherein each R$_{10}$ is independently —H; straight chained or branched C$_1$–C$_7$ alkyl; straight chained or branched C$_2$–C$_7$ alkenyl or alkynyl; and wherein X is independently CH$_2$, O, NH or S; or a pharmaceutically acceptable salt thereof.

5. An (−) enantiomer of the compound of claim 4.
6. An (+) enantiomer of the compound of claim 4.
7. The compound of claim 4 having the structure:

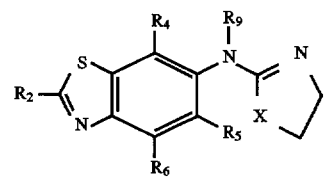

8. A pharmaceutical composition comprising a therapeutically effective amount of the compound of claim 1 or 4 and a pharmaceutically acceptable carrier.

9. The compound of claim 1 having the structure:

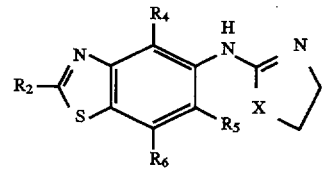

10. The compound of claim 9 having the structure:

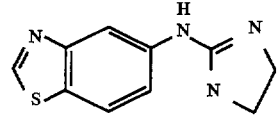

11. The compound of claim 1 having the structure:

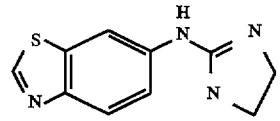

12. The compound of claim 7 having the structure:

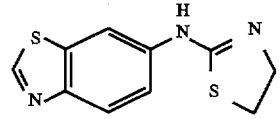

13. A method for anaesthetic premedication which comprises administering to the subject an amount of the compound of claim 1 or 4 effective to reduce in the subject the requirement for anaesthetic drugs.

14. A method of treating a subject suffering from a disorder associated with elevated intraocular pressure which comprises administering to the subject an amount of the compound of claim 1 or 4 effective to lower the subject's intraocular pressure.

15. A method of treating a disease which is susceptible to treatment by agonism of the $\alpha_2$ adrenergic receptor which comprises administering to the subject an amount of the compound of claim 1 or 4 effective to treat the disease.

16. A method of treating a subject suffering from pain which comprises administering to the subject an amount of the compound of claim 1 or 4 effective to treat the subject's pain.

\* \* \* \* \*